United States Patent [19]

Hegar

[11] 4,092,308

[45] May 30, 1978

[54] 4-SULPHOMETHYL SUBSTITUTED HYDROXYPYRIDONE AZO DYESTUFFS

[75] Inventor: Gert Hegar, Schonenbuch, Switzerland

[73] Assignee: Ciba-Geigy Corporation, Ardsley, N.Y.

[21] Appl. No.: 736,930

[22] Filed: Oct. 29, 1976

Related U.S. Application Data

[63] Continuation of Ser. No. 604,402, Aug. 13, 1975, abandoned, which is a continuation of Ser. No. 396,914, Sep. 13, 1973, abandoned.

[30] Foreign Application Priority Data

Oct. 5, 1972 Switzerland .................. 14561/72
Aug. 20, 1973 Switzerland .................. 11966/73

[51] Int. Cl.² ............... C09B 29/36; C09B 62/08; C09B 62/24; C09B 62/50
[52] U.S. Cl. ........................ 260/153; 260/146 R; 260/146 D; 260/146 T; 260/154; 260/155; 260/156; 260/294.8 R
[58] Field of Search ............. 260/156, 153, 154, 155

[56] References Cited

U.S. PATENT DOCUMENTS

| 2,857,372 | 10/1958 | Straley et al. ............ 260/156 X |
| 3,109,840 | 11/1963 | Beffa et al. ............... 260/156 |
| 3,619,112 | 11/1971 | Berrie et al. ............ 260/156 X |
| 3,640,674 | 2/1972 | Berrie et al. ............... 260/156 |
| 3,657,214 | 4/1972 | Berrie et al. ............... 260/156 |

FOREIGN PATENT DOCUMENTS

| 2,141,453 | 2/1972 | Germany ................... 260/156 |
| 1,122,389 | 8/1968 | United Kingdom ......... 260/156 |

Primary Examiner—Charles F. Warren
Attorney, Agent, or Firm—Edward McC. Roberts; Michael W. Glynn; Prabodh I. Almaula

[57] ABSTRACT

Azo compounds of the formula

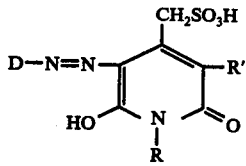

wherein R represents a hydrogen atom, an alkyl or aryl radical, R' represents a hydrogen or halogen atom, a cyano, carboxylic amide, alkylsulphonyl, arylsulphonyl, nitro, nitroso, amino, or acylamino group, and D represents the radical of a diazo component, are valuable dyestuffs for the dyeing of textile materials.

4 Claims, No Drawings

4-SULPHOMETHYL SUBSTITUTED HYDROXYPYRIDONE AZO DYESTUFFS

This is a continuation of application Ser. No. 604,402 filed Aug. 13, 1975 (now abandoned) which in turn was a continuation of application Ser. No. 396,914 filed on Sept. 13, 1973 and now abandoned.

The invention relates to azo compounds of the formula

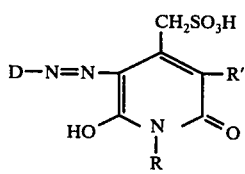

wherein R represents a hydrogen atom, an alkyl or aryl radical, R' represents a hydrogen or halogen atom, a cyano, carboxylic amide, alkylsulphonyl, arylsulphonyl, nitro, nitroso, amino, or acylamino group, and D represents the radical of a diazo component. The diazo radical is a heterocyclic or aromatic radical which can itself contain an azo group or which is derived from a compound of the anthraquinone, nitroaryl, phthalocyanine, or stilbene series or the like. The diazo radical is in particular a radical of the benzene or naphthalene series.

The azo compounds of the formula (1) can exist in a number of tautomeric forms. In order to simplify the description the compounds in the formulae are illustrated in only one of these tautomeric forms, but it must be expressly emphasised that throughout this specification, especially in the claims, the description always refers to compounds in any of these tautomeric forms.

In particular, the term "pyridone" is intended to include also the compounds in question which are substituted at the nitrogen atoms of the pyridone ring by a hydrogen atom as well as the corresponding tautomeric 2,6-dihydroxypyridones.

In addition to the sulphomethyl group, the azo compounds according to the invention can be free from water-solubilising groups such as sulphonic acid groups, carboxyl groups, or quaternised amino groups; in particular, however, they can also contain such groups. Above all, the compounds can contain one or more than one reactive radical, for example, a halotriazine radical, in the molecule. In addition to being substituted by water-solubilising groups, the azo compounds can be substituted in the normal way, by still further atoms or groups of atoms, and in particular both in the radical of the diazo component and in the radicals R and R', for example by halogen atoms or hydroxy, amino, alkyl, aryl, alkoxy, aryloxy, acylamino, cyano, acyl, carbalkoxy, acyloxy or nitro groups, and the like. If the radical of the diazo component contains, in the ortho-position to the azo bridge, a complex-forming group, for example, a hydroxyl, amino or carboxyl group or an alkoxy group, for example a methoxy group, the compounds in question can optionally be converted into their heavy metal complex compounds either before the introduction of reactive radicals or afterwards.

Possible complex-forming metals are, for example, iron, manganese, nickel, copper, cobalt and chromium. The heavy metal complexes can contain one or two molecules of azo compounds containing the radical of the formula (1), bonded to a metal atom (1:1- or 1:2-complexes). However, in 1:2-complexes one of the two ligand molecules can also be an azo compound which does not correspond to the formula (1), that is to say, for example, a compound of the azobenzene type which contains corresponding complex-forming groups.

Groupings capable of reactive with the hydroxyl groups of cellulose or with the amino groups of polyamides to form a covalent chemical bond are possible reactive radicals. Such a grouping is, in particular, a low molecular alkanoyl or alkylsulphonyl radical substituted by a removable atom or a removable group, a low molecular alkenoyl or alkenesulphonyl radical optionally substituted by a removable atom or a removable group, a carboxylic or heterocyclic radical containing 4-, 5- or 6-rings which is substituted by a removable atom or a removable group and is bonded via a carbonyl or sulphonyl group, or a triazine or pyrimidine radical substituted by a removable atom or a removable group and directly bonded via a carbon atom, or such a grouping contains such a radical. The reactive radical is preferably a six-membered heterocyclic radical which is bonded via an amino group and contains halogen atoms, for example a halotriazine or halopyrimidine radical.

In particular, the fibre-reactive radical is a radical of the formula $-N(R_1)-Z$, wherein $R_1$ represents a low molecular alkyl radical or preferably a hydrogen atom, and Z represents a dihalotriazine radical or a monohalotriazine radical. By low molecular alkyl radicals are meant in this context alkyl radicals with up to 4 carbon atoms, e.g. the methyl, ethyl, propyl, isopropyl, or butyl radical.

The invention relates in particular to azo compounds of the formula (1) wherein R represents a hydrogen atom or an alkyl radical with 1 to 4 carbon atoms, R' represents a hydrogen or halogen atom, a cyano or carboxylic amide group, and D represents the radical of a diazo component of the benzene or naphthalene series. The invention also to azo compounds of the formula (1) which contain fibre-reactive radicals, above all cyclic fibre-reactive radicals, e.g. triazine, pyrimidine, or cyclobutane radicals; these fibre-reactive radicals can also be contained in the substituents R and R'.

A special group of azo compounds of the formula (1) is that of the formula

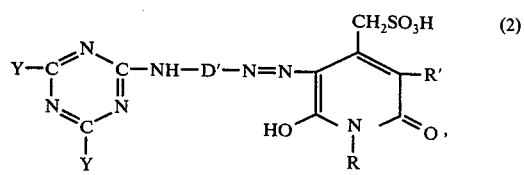

wherein D' represents a sulphobenzene radical, one Y represents a halogen atom and the other Y represents a halogen atom or an amino group to which a fibre-reactive radical can be bonded, an alkoxy, phenoxy, alkylmercapto, or arylmercapto group, and wherein R' has the meaning given in the explanation of the formula (1). In addition to one or two sulphonic acid groups, the benzene radical D', as already mentioned, can carry further substituents, in particular complex-forming groups.

Particularly valuable compounds are those of the formula (2), wherein D' represents a monosulphobenzene radical, especially one which is addition to a sulphonic acid group carries on further substituents, one Y represents a halogen atom, and the other Y represents a mono- or disulphophenylamino, or mono- or disulphonaphthylamino group or an alkoxy group, R represents a hydrogen atom, a methyl or ethyl radical, and R' represents the cyano group.

A further group of interesting azo compounds of the formula (1) is that of the formula

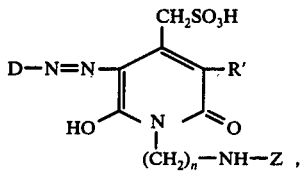
(3)

wherein D represents the radical of a diazo component of the benzene or naphthalene series, in particular one that contains water-solubilising substituents, R' represents a hydrogen or halogen atom, a cyano, carboxylic amide, alkylsulphonyl, arylsulphonyl, nitro, nitroso, amino, or acylamino group, Z represents a fibre-reactive radical, especially a dihalotriazine radical or a monohalotriazine radical, which contains an amino, alkoxy, phenoxy, alkylmercapto, or arylmercapto group bonded to a carbon atom, and $n$ is a positive whole number, preferably between 1 and 4.

Importance attaches also to azo compounds of the formula (1), which each contain one fibre-reactive radical in the diazo and coupling component, for example compounds of the formula (3), which in addition to the reaction radical Z or the mono- or dihalotriazine radical contain a further reactive radical in the diazo component D.

The manufacture of the azo compounds of the formula (1) is carried out by coupling and, optionally, by metallisation and/or acylation, in order to introduce a reactive radical.

The process consists on coupling a diazo component of the formula D-NH$_2$(4), in particular one belonging to the benzene series, with a 4-sulphomethyl-6-hydroxy-pyridone-(2) of the formula

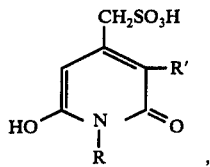
(5)

wherein R and R' have the meanings given in the explanation of the formula (1), and metallising the resulting azo compound optionally with a heavy metal donor and/or acylating it with an acylating agent. Preferably there are used as starting materials diazo components which contain a fibre-reactive radical and a water-solubilising group.

In particular there are used diazo components of the benzene or naphthalene series and coupling components of the formula (5), wherein R represents a hydrogen atom or an alkyl radical with 1 to 4 carbon atoms, and R' represents a hydrogen or halogen atom, a cyano or carboxylic amide group.

The preferred azo compounds of the formula (2) are manufactured by coupling a diazo component of the formula

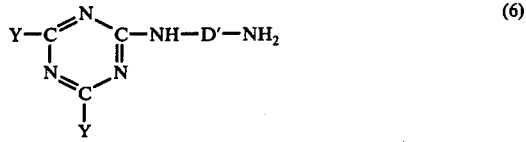
(6)

with a coupling component of the formula (5), Y, D', R, and R' having the same meanings as given in the explanation of the formula (2), to give an azo compound of the formula (2), or by coupling a diazo component of the formula

V-D'-NH$_2$ (7)

with a coupling component of the formula (5), V representing a H$_2$N group or a group which can be converted into a H$_2$N group by reduction or saponification, and D', R, and R' have the meanings given hereinabove, to give an azo compound of the formula

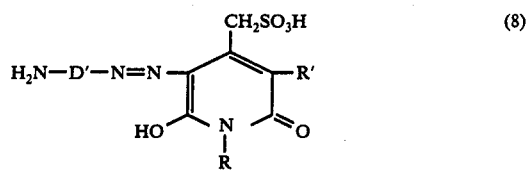
(8)

and the resulting azo compound of the formula (8) is acylated with a halo-s-triazine of the formula

(9)

in which two of the symbols Y represent halogen atoms and the third Y represents a halogen atom or an amino, alkoxy, phenoxy, alkylmercapto, or arylmercapto group, to give an azo compound of the formula (2).

Particularly important starting materials are diazo components of the formulae (6) and (7), wherein D' represents a monosulphobenzene radical, one Y represents a halogen atom and the other Y represents a mono- or disulphophenylamino, mono- or disulphonaphthylamino group or an alkoxy group, coupling components of the formula (5), wherein R represents a hydrogen atom, a methyl or ethyl group, and R' represents the cyano group, and halo-s-triazines of the formula (9), wherein two symbols Y represent halogen atoms and the third Y represents a mono- or disulphophenylamino, mono- or disulphonaphthylamino group or an alkoxy group.

A suitable group V in formula (7) is in particular the acetylamino group or the nitro group.

The diazotisation is carried out by methods which are in the themselves known, for example by means of hydrochloric acid and sodium nitrite. The coupling with the pyridone is also carried out according to methods which are in themselves known, in an acid to weakly alkaline medium.

Depending on the solubility of the components, the reaction with the heavy metal donor is carried out according to conventional methods in various solvents, for example water, ethanol, formamide, glycolethers, pyridine and the like, optionally at elevated temperature, and in a weakly acid to alkaline medium.

Instead of a compound of the formula (5) which is unsubstituted in 5-position, it is also possible to use as coupling component a compound which contains bonded in 5-position a group which can be removed under the conditions of the coupling reaction or a removable atom, by which means a coupling in 5-position is made possible. Such coupling components correspond therefore to the formula

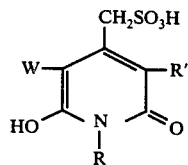

(10)

wherein R represents a hydrogen atom, an alkyl or aryl radical, R' represents a hydrogen atom or halogen atom, a cyano, carboxylic amide, alkylsulphonyl, arylsulphonyl, nitro, nitroso, amino, or acylamino group, and W represents a radical which can be removed during the coupling reaction.

Examples of radicals which can be removed during the coupling are carboxylic amide, carboxylic ester, sulphonamide, sulphonic ester, sulphonylcarbonyl, alkylcarbonyl, or arylcarbonyl groups. Possible removable radicals W are in particular carboxylic amide radicals.

As diazo components which can be used for the manufacture of the azo compounds of the formula (1), or of the corresponding heavy metal complexes, there may be cited the diazo compounds of the following amines:
aminobenzene,
1-amino-4-chlorobenzene,
1-amino-4-bromonbenzene,
1-amino-4-methylbenzene,
1-amino-2-nitrobenzene,
1-amino-4-nitrobenzene,
1-amino-4-cyanobenzene,
1-amino-2,5-dicyanobenzene,
1-amino-4-methylsulphonylbenzene,
1-amino-4-carbalkoxybenzene,
1-amino-2,4-dichlorobenzene,
1-amino-2,4-dibromobenzene,
1-amino-2-methyl-4-chlorobenzene,
1-amino-2-trifluoromethyl-4-chlorobenzene,
1-amino-2-cyano-4-chlorobenzene,
1-amino-2-carbomethoxy-4-chlorobenzene,
1-amino-2-carbomethoxy-4-nitrobenzene,
1-amino-2-chloro-4-cyanobenzene,
1-amino-2-chloro-4-nitrobenzene,
1-amino-2-bromo-4-nitrobenzene,
1-amino-2-chloro-4-carboethoxybenzene,
1-amino-2-chloro-4-methylsulphonylbenzene etc.

As coupling components there may be cited:
1-ethyl-3-cyano-4-sulphomethyl-6-hydroxypyridone-(2),
1-phenyl-3-cyano-4-sulphomethyl-6-hydroxypyridone-(2),
1-methyl-3-aminocarbonyl-4-sulphomethyl-6-hydroxypyridone-(2),
1-ethyl-4-sulphomethyl-6-hydroxypyridone-(2),
2,6-dihydroxy-4-sulphomethyl-pyridine,
1-(2'-acetylaminoethyl)-3-cyano-4-sulphomethyl-6-hydroxy-pyridone-(2),
1-benzyl-3-aminocarbonyl-4-sulphomethyl-6-hydroxypyridone-(2),
1-methyl-3-chloro-4-sulphomethyl-6-hydroxypyridone-(2),
1-isopropyl-3-cyano-4-sulphomethyl-6-hydroxypyridone-(2),
1-(2'-hydroxyethyl)-3-cyano-4-sulphomethyl-6-hydroxypyridone-(2),
1-(4'-methoxyphenyl)-3-aminocarbonyl-4-sulphomethyl-6-hydroxy-pyridone-(2),
1-(2'-chloroethyl)-3-cyano-4-sulphomethyl-6-hydroxypyridone-(2),
1-butyl-3-nitroso-4-sulphomethyl-6-hydroxypyridone-(2),
1-ethyl-3-aminocarbonyl-4-sulphomethyl-6-hydroxypyridone-(2),
1-methyl-4-sulphomethyl-6-hydroxypyridone-(2),
1-ethyl-3-methylsulphonyl-4-sulphomethyl-6-hydroxypyridone-(2),
2,6-dihydroxy-3-aminocarbonyl-4-sulphomethylpyridine,
3-acetylamino-4-sulphomethyl-2,6-dihydroxypyridine,
1-ethyl-3-nitro-4-sulphomethyl-6-hydroxypyridone-(2),
1-isopropyl-3-chloro-4-sulphomethyl-6-hydroxypyridone-(2),
1-ethyl-3-bromo-4-sulphomethyl-6-hydroxypyridone-(2),
1-(4'-chlorophenyl)-4-sulphomethyl-6-hydroxypyridone-(2),
1-(4'-acetaminophenyl)-4-sulphomethyl-6-hydroxypyridone-(2),
1-phenyl-3-aminocarbonyl-4-sulphomethyl-6-hydroxypyridone-(2),
1-methyl-3-cyano-4-sulphomethyl-6-hydroxypyridone-(2),
2,6-dihydroxy-3-cyano-4-sulphomethyl-pyridine,
1-phenyl-3-acetylamino-4-sulphomethyl-6-hydroxypyridone-(2),
1-benzyl-3-nitroso-4-sulphomethyl-6-hydroxypyridone-(2).

The coupling components of the formula (5) are manufactured by reacting a haloacetoacetic ester, e.g. a chloroacetoacetic ester, with a sulphite, e.g. sodium sulphite, and condensing the resulting sulphoacetoacetic ester with an α-substituted acetic amide, e.g. cyanoacetic-N-ethylamide. The desired 4-sulphomethyl-2,6-dihydroxypyridine or 6-hydroxypyridone-(2) is obtained accompanied by the splitting off of water and of a hydroxy compound correpondinf to the ester group of the starting material. In the case of the above mentioned cyanoacetic-N-ethylamide there is obtained consequently 1-ethyl-3-cyano-4-sulphomethyl-6-hydroxypyridone-(2), in which the cyano group can be saponified to the carboxylic amide group.

Hydrolytic removal of the carboxylic amide group yields the 1-ethyl-4-sulphomethyl-6-hydroxy-pyridone-(2), which is unsubstituted in 3-position and in which other substituents can be introduced by further reactions.

Coupling components of the formula (10), which contain a halogen atom bonded in 3-position, can be obtained for example by chlorination of the corresponding 4-sulphomethyl-5-carbonamido-6-hydroxypyridone-(2), which is unsubstituted in 3-position.

The removal of a substituent in 5-position can also take place advantageously not later than during the coupling, so that — as already stated — hydroxypyridones of the formula (10) which are substituted in 5-position can come into direct consideration as coupling components.

Azo compounds of formula (1), or the corresponding heavy metal complexes, which contain one or more reactive groups, can be manufactured by using diazo or coupling components which already contain reactive groups. However, in many cases it is possible to introduce reactive groups subsequently into the azo compounds. The introduction can be effected after the coupling or metallisation.

The introduction of the reactive radical is preferably effected by acylating corresponding aminoazo compounds or coupling components which contain an acylatable amino group, or corresponding diazo components, which, in addition to the amino group to be diazotised, still contain a further acylatable amino group, or a group which can be converted into an acylatable amino group, for example by reduction or saponification, for example the nitro group or the acylamino group.

Corresponding diazo components which, as described above, are suitable for introducing a reactive radical, are, for example:

1,3-diaminobenzene-4-sulphonic acid
1,3-diaminobenzene-4,6-disulphonic acid
1,4-diaminobenzene-2-sulphonic acid
1,4-diaminobenzene-2,5- or 2,6-disulphonic acid
1-amino-4-nitrobenzene
1-amino-2-chloro-4-nitrobenzene
1,3-diamino-4-methylbenzene-6-sulphonic acid
6-acetylamino-5-chloro-2-aminophenol
6-nitro-4-methyl-2-aminophenol
4-nitro-2-aminophenol-6-sulphonic acid
6-acetylamino-1-amino-2-naphthol-4-sulphonic acid
and other compounds, for example those mentioned in the list of possible diazo components.

Examples of aminoazo compounds into which the fibre-reactive radicals can be introduced after the coupling are the coupling products of the diazo components cited hereinabove with corresponding pyridones.

If the reactive radical contains still further readily removable substituents, for example halogen atoms, as in the dichlorotriazine radical, then it can be condensed with compounds which contain a reactive hydrogen atom which is bonded via a heteroatom and is able to react with a removable substituent of the reactive radical to form a functional group which is bonded via the heteroatom. In this way especially a chlorine atom in the dichlorotriazine radical can be replaced by one of the corresponding radicals by reaction with ammonia, an amine, an alcohol, a phenol or mercaptan.

Instead of subsequently replacing a halogen atom in a dihalotriazine radical by an amino, alkoxy, aryloxy group or a mercapto group, it is also possible to use as fibre-reactive acylating agent a dihalotriazine which already contains an amino, alkoxy, aryloxy or mercapto group bonded to the triazine ring.

Further important azo compounds are those of the formula (1) which contain a monohalotriazine radical which is bonded via an amino group and which in addition to the halogen atom contains an amino group bonded to the triazine ring, with a further fibre-reactive radical, especially a halotriazine radical, being bonded to this amino group. If the second, additional fibre-reactive radical is a halotriazine radical, it is bonded preferably via the radical of an alkylenediamine or arylenediamine to the first triazine radical. The fibre-reactive amino group which is present in the monohalotriazine radical in addition to the halogen atom therefore preferably has the structure

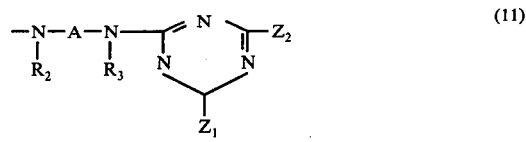

wherein $R_2$ and $R_3$ represent a hydrogen atom or a low molecular alkyl radical, A represents an alkylene or arylene radical, $Z_1$ represents a halogen atom, e.g. a fluorine, chlorine, or bromine atom, and $Z_2$ represents a halogen atom, an amino, alkoxy, aryloxy, alkylmercapto or arylmercapto group. Low molecular alkyl radicals are to be understood as meaning in this context alkyl radicals with 1 to 4 carbon atoms. A can be an alkylene radical with short or long chain, for example an ethylene or a hexylene radical; but preferably A is a benzene radical, for example a m-phenylene or p-phenylene radical, especially a phenylenesulphonic acid radical.

Suitable alkoxy groups are radicals of primary, secondary, or tertiary alcohols, for example the methoxy, ethoxy, propyloxy, isopropoxy, or 1,1-dimethylethoxy group, radicals of etherified dialcohols, for example the ethoxyethoxy or methoxypropyloxy group, radicals of unsaturated aliphatic alcohols, for example the allyloxy or propargyloxy group, or radicals of aliphatic alcohols which contain cyclic groups, for example the benzyloxy, furfuryloxy or tetrahydrofurfuryloxy group. As aryloxy groups there may be cited radicals of phenols and naphthols, especially the phenoxy, sulphophenoxy or disulphophenoxy group. As alkylmercapto or arylmercapto groups there may be mentioned the methylmercapto and phenylmercapto groups.

In a particular embodiment of the invention, $Z_2$ is the chromogenic radical of the compounds of the formula (1).

The acylations with the fibre-reactive acylating agents and the condensation with compounds which contain a reactive hydrogen atom bonded via a heteroatom are advantageously carried out with the use of acid acceptors, such as sodium carbonate or sodium hydroxide, and under such conditions that there still remain in the fibre-reactive radical of the finished product replaceable halogen atoms, unsaturated bonds or the like, i.e. these reactions are carried out for example in organic solvents or at relatively low temperatures in aqueous media.

Suitable acylating agents which contain a reactive radical are in particular the halides or anhydrides of organic acids which contain readily removable atoms or groups of atoms.

As examples of acylating agents which contain a fibre-reactive radical there may be cited the following:
chloro- or bromoacetyl chloride
β-chloro- or β-bromopropionyl chloride
α,β-dichloro- or α,β-dibromopropionyl chloride
chloromaleic anhydride
carbyl sulphate
acrylic chloride 4,5-dichloro-1-phenylpyridazonecarboxylic or sulphonic acid chloride
4,5-dichloropyridazopropionic acid chloride 1,4-dichlorophthalazinecarboxylic or sulphonic acid chloride 2,3-dichloroquinoxalinecarboxylic or sulphonic acid chloride 2,4-dichloroquinazolinecarboxylic or sulphonic acid chloride 2-methanesulphonyl-4-chloro-6-methylpyrimidine 2,4-bis-methanesulphonyl-6-methylpyrimidine 2,4,6-trichloropyrimidine or 2,4,5,6-tetrachloropyrimidine 2,4,6-tribromopyrimidine or 2,4,5,6-tetrabromopyrimidine 2-methanesulphonyl-4,5-dichloro-6-methylpyrimidine 2,4,6-trichloro-5-bromopyrimidine 2,4,5,6-tetrafluoropyrimidine 4,6-difluoro-5-chloropyrimidine 2,4,6-trifluoro-5-chloropyrimidine 2,4,5-trifluoropyrimidine 2,4,6-trichloro-(tribromo- or trifluoro-)1,3,5-triazine, and 4,6-dichloro-(dibromo- or difluoro-)1,3,5-triazines, which are substituted in 2-position cyan aryl or alkyl radical, e.g. a phenyl, methyl or ethyl radical, or by the radical of an aliphatic or aromatic mercapto compound which is bonded via the sulphur atom or of a hydroxyl compound which is bonded via the oxygen atom, or especially by a $NH_2$ group or by the radical of an aliphatic, heterocyclic or aromatic amino compound which is bonded via the nitrogen atom.

The condensation with the acid halides or anhydrides, or with the heterocyclic halogen compounds, is advantageously carried out in the presence of acid acceptors, for example sodium carbonate. It is to be understood that all these reactions are to be carried out in such a manner that an unsaturated bond or at least a replaceable halogen atom still remains in the final product.

The azo compounds obtainable according to the present process and its different variants, as well as their heavy metal complexes, are new; they are suitable for dyeing and printing widely different types of materials, such as, for example, silk, leather, wool, synthetic fibres of polyamides and polyurethanes, polyhydroxylated materials, for example cellulose-containing materials of fibreous structure, such as linen, cellulose, regenerated cellulose, cotton and the like.

The non-metallised azo compounds according to the invention are particularly important as dyestuffs.

However, the most important compounds are those azo compounds according to the invention which contain a reactive radical and a water-solubilising group, in particular a sulphonic acid group. These dyestuffs are preferably used for dyeing nitrogen-containing fibres, such as, for example, of super polyamides, super polyurethanes, silk, leather and in particular wool, for example from weakly acid, neutral or weakly alkaline baths, optionally with the addition of customary assistants, for example ethylene oxide condensation products of high molecular weight amines, and, above all, for dyeing cellulose materials, in particular cotton, for example by the exhaustion process from a dilute liquor, from alkaline baths optionally having a high salt content, and in particular by the pad-dyeing process, in which the article is impregnated with aqueous dyestuff solutions which optionally also contain salt, and the dyestuffs are fixed after an alkali treatment or in the presence of alkali, optionally with the action of heat.

The water-soluble reactive dyestuffs according to the invention show an excellent build-up capacity. They are also suitable for printing, in particular on cotton, and also for printing nitrogen-containing fibres, for example of wool, silk or fibre blends containing wool.

The dyeings and prints are distinguished by interesting and valuable, very pure and brilliant shades. The dyeings and prints exhibit a good stability to acids and alkalies, and a good stability to synthetic resin finishing agents, have a good fastness to light and, in particular on cotton, an outstanding fastness to wet processing. The high degree of fixation and the easy removability of nonfixed dyestuff is also deserving of mention.

In order to improve the fastness to wet processing, it is advisable to rinse the dyeings and printings obtained thoroughly with cold and hot water, optionally with the addition of an agent which has a dispersing effect and promotes the diffusion of the non-fixed material.

In the examples which follow, the parts, unless otherwise indicated, denote parts by weight, and the percentages denote percentages by weight. The relationship of parts by weight to parts by volume is the same as of the gram to the $cm^3$.

EXAMPLE 1

A solution of 18.5 parts of cyanuric chloride in 50 parts of acetone is poured into a neutralised solution of 17.3 parts of 1-aminobenzene-3-sulphonic acid in 100 parts of water and 100 parts of ice and during the condensation the pH is maintained at 6 to 7 by the dropwise addition of 2N sodium hydroxide solution. Upon completion of the condensation a neutral solution of 18.8 parts of 1,3-diaminobenzene-4-sulphonic acid is added, the solution is heated to 20°–25° C and the pH maintained is at 6 to 7 by the dropwise addition of 2N sodium hydroxide solution. As soon as no more diaminobenzenesulphonic acid can be detected in the mixture, 7 parts of sodium nitrite are added and when this has dissolved, the solution is poured on a mixture of 200 parts of ice and 25 parts of concentrated hydrochloric acid. The yellow suspension of the diazo compound is stirred for 1 hour in an ice bath, then a slight excess of nitrous acid is annulled by the addition of sulphamic acid. A solution of 25.8 parts of 1-ethyl-3-cyano-4-sulphomethyl-6-hydroxypyridone-(2) in 100 parts of water is then poured into this diazo solution. The pH, which is initially 1.5, is raised to 6.5 by the dropwise addition of sodium hydroxide solution, when a clear yellow solution is obtained. This solution is stirred for 1 hour in an ice bath, the pH is adjusted to 7, and the dyestuff is precipitated by addition of sodium chloride. The resulting dyestuff dyes cotton in pure yellow shades.

Further yellow dyestuffs are obtained when, in accordance with the directions of Example 1, the amines listed in column 1 of the following Table are condensed with cyanuric chloride, the resulting monocondensation products are condensed with the diamines listed in column II, diazotised, and coupled with the coupling components listed in column III.

| | I<br>Amine | II<br>Diamine | III<br>Coupling Component |
|---|---|---|---|
| 1 | 1-aminobenzene-3-sulphonic acid | 1,3-phenylendiamine-4-sulphonic acid | 1-phenyl-3-cyano-sulphomethyl-6-hydroxypyridone-2 |
| 2 | " | " | 1-methyl-3-aminocarbonyl-4-sulphomethyl-6-hydroxypyridone-2 |
| 3 | 1-aminobenzene-2-sulphonic acid | " | 1-ethyl-4-sulphomethyl-6-hydroxypyridone-2 |
| 4 | " | " | 2,6-dihydroxy-4-sulphomethyl-pyridine |
| 5 | " | " | 1-(2'-acetylaminoethyl)-3-cyano-4-sulphomethyl-6-hydroxypyridone-2 |
| 6 | 1-aminobenzene-4-sulphonic acid | " | 1-benzyl-3-aminocarbonyl-4-sulphomethyl-6-hydroxypyridone-2 |
| 7 | " | " | 1-methyl-3-chloro-4-sulphomethyl-6-hydroxypyridone-2 |
| 8 | 1-aminobenzene-2,4-disulphonic acid | " | 1-isopropyl-3-cyano-4-sulphomethyl-6-hydroxypyridone-2 |
| 9 | 1-aminobenzene-2,5-disulphonic acid | 1,4-phenylenediamine-2-sulphonic acid | 2,6-dihydroxy-4-sulphomethylpyridine |
| 10 | 1-aminobenzene-3,5-disulphonic acid | 1,3-phenylenediamine | 1-(2'-hydroxyethyl)-3-cyano-4-sulphomethyl-6-hydroxypyridone-2 |
| 11 | 1-naphthylamine-5-sulphonic acid | 1,3-phenylenediamine-4,6-disulphonic acid | 1-(4'-methoxyphenyl)-3-aminocarbonyl-4-sulphomethyl-6-hydroxypyridone-2 |
| 12 | 1-naphthylamine-6-sulphonic acid | " | 1-ethyl-4-sulphomethyl-6-hydroxypyridone-2 |
| 13 | 1-naphthylamine-7-sulphonic acid | " | 1-(2'-chloroethyl)-3-cyano-4-sulphomethyl-6-hydroxypyridone-2 |
| 14 | 1-naphthylamine-5,7-disulphonic acid | 1,4-phenylenediamine-2,5-disulphonic acid | 2,6-dihydroxy-4-sulphomethylpyridine |
| 15 | 4-aminobenzyl-sulphonic acid | 1,3-phenylenediamine-4-sulphonic acid | 1-butyl-3-nitroso-4-sulphomethyl-6-hydroxypyridone-2 |
| 16 | 2-amino-5-sulphobenzoic acid | " | 1-ethyl-4-sulphomethyl-6-hydroxypyridone-2 |
| 17 | 4-aminobenzoic acid | 1,3-phenylenediamine-4,6-disulphonic acid | 1-ethyl-3-cyano-4-sulphomethyl-6-hydroxypyridone-2 |
| 18 | 2-aminobenzoic acid | " | 1-ethyl-3-aminocarbonyl-4-sulphomethyl-6-hydroxypyridone-2 |
| 19 | 1-aminobenzene-3-and-4-sulphonic acid | 1,3-phenylenediamine-4-sulphonic acid | 1-methyl-4-sulphomethyl-6-hydroxypyridone-2 |
| 20 | 1-aminobenzene-4-β-chloroethyl-sulphone | " | 1-ethyl-3-methylsulphonyl-4-sulphomethyl-6-hydroxypyridone-2 |
| 21 | 1-amino-3-chloro-acetylaminomethyl-benzene-6-sulphonic acid | " | " |
| 22 | aniline-N-ω-methane-sulphonic acid | " | " |
| 23 | 3'-amino-2,4-bis-phenylamino-6-chloro-1,3,5-triazine''-sulphonic acid | 1,3-phenylenediamine-4-sulphonic acid | 1-ethyl-3-aminocarbonyl-4-sulphomethyl-6-hydroxypyridone-2 |
| 24 | 3'-amino-2,4-bis-phenylamino-6-chloro-1,3,5-triazine-4',3''-disulphonic acid | " | " |

EXAMPLE 2

9.4 Parts of 1,3-diaminobenzene-4-sulphonic acid are suspended in 100 parts of water and dissolved by addition of alkali to a pH of 7. To this solution are added at room temperature and with good stirring 10.4 parts of 2-isopropoxy-4,6-dichloro-1,3,5-triazine and the pH is maintained at 6-7 during the condensation by the dropwise addition of 2N sodium hydroxy solution.

Upon completion of the condensation, the condensation mixture is cooled to 0° C, 13 parts by volume of concentrated hydrochloric acid are added, and diazotisation is carried out by the dropwise addition of 50 parts of n-sodium nitrite solution. A solution of 13.5 parts of the sodium salt of 2,6-dihydroxy-3-aminocarbonyl-4-sulphomethylpyridine in 60 parts of water is poured into the resulting diazo suspension and the coupling mixture is adjusted to pH 7 by the dropwise addition of 5N sodium hydroxide solution within 1 hour. The dyestuff is isolated from the yellow dyestuff solution by addition of potassium chloride. It dyes cotton in fast yellow shades.

Further yellow dyestuffs having similar properties are obtained if the compound listed in column II of the following Table is used as diamine, that listed in column I as acylating agent, and that listed in column III as coupling component.

|    | I | II | III |
|----|---|----|-----|
| 1  | 2,4-dichloro-6-methoxy-1,3,5-triazine | 1,3-phenylene-diamine-4-sulphonic acid | 1-ethyl-3-aminocarbonyl-4-sulphomethyl-6-hydroxypyridone-2 |
| 2  | 2-amino-4,6-dichloro-1,3,5-triazine | " | 4-sulphomethyl-2,6-dihydroxypyridine |
| 3  | 2-(2'-ethoxy)-ethoxy-4,6-dichloro-1,3,5-triazine | " | 1-ethyl-3-cyano-4-sulphomethyl-6-hydroxypyridone-2 |
| 4  | 2,4,5,6-tetra-chloropyrimidine | " | " |
| 5  | 2,3-dibromopropionic chloride | 1,4-phenylene-diamine-3-sulphonic acid | 1-methyl-3-aminocarbonyl-4-sulphomethyl-6-hydroxypyridone-2 |
| 6  | 2,4-dichloropyrimidine-5-carboxylic acid chloride | 2,4-diamino-5-sulpho benzoic acid | 4-sulphomethyl-2,6-dihydroxypyridine |
| 7  | 2,4-dichloro-6-phenyl-1,3,5-triazine | 1,3-diamino-benzene-4,6-disulphonic acid | " |
| 8  | 2,4-dichloro-6-[5'-(4''-chloro-6''-amino)-1,3,5-triazine-2''-yl-amino]-phenyl-amino-1,3,5-triazine-2'-sulphonic acid | 1,3-phenylene-diamine-4-sulphonic acid | " |
| 9  | chloroacetyl chloride | " | 1-phenyl-3-cyano-4-sulphomethyl-6-hydroxypyridone-2 |
| 10 | α-bromoacrylic chloride | " | 1-methyl-4-sulphomethyl-6-hydroxypyridone-2 |
| 11 | 3,5-dinitro-4-chlorobenzene-sulphonic acid chloride | 1,3-diamino-benzene-4,6-disulphonic acid | " |
| 12 | 2,2,3,3-tetrafluorocyclobutane-1-carboxylic acid chloride | " | 3-acetylamino-4-sulphomethyl-2,6-dihydroxypyridine |
| 13 | β-chloroethyl-sulphonyl-endo-methylene-cyclohexanecarboxylic acid chloride | 2,4-diamino-toluene-5-sulphonic acid | 1-benzyl-3-aminocarbonyl-4-sulphomethyl-6-hydroxypyridone-2 |
| 14 | 2-chlorobenzthiazole-carboxylic acid chloride | 1,4-diamino-5-chlorobenzene-2-sulphonic acid | " |
| 15 | 4,5-dichloropyridazone-propionic chloride | 1,4-diamino-benzene-2,5-disulphonic acid | 1-ethyl-3-nitro-4-sulphomethyl-6-hydroxypyridone-2 |
| 16 | 2,3-dichloro-quinoxaline-6-sulphonic acid chloride | 1,4-diamino-benzene-2,6-disulphonic acid | 1-isopropyl-3-chloro-4-sulphomethyl-6-hydroxypyridone-2 |
| 17 | 2-methanesulphonyl-4-chloro-6-methyl-pyrimidine | " | 1-ethyl-3-bromo-4-sulphomethyl-6-hydroxypyridone-2 |
| 18 | 2,4,6-tribromo-pyrimidine | 1,3-diamino-benzene-4-sulphonic acid | 1-ethyl-3-aminocarbonyl-6-hydroxpyridone-2 |
| 19 | 2-methanesulphonyl-4,5-dichloro-6-methyl-pyrimidine | " | 1-ethyl-3-aminocarbonyl-4-sulphomethyl-6-hydroxypyridone-2 |
| 20 | 5-cyano-2,4,6-trichloro-pyrimidine | " | " |
| 21 | 2,6-bismethanesulphonylpyridine-4-carboxylic acid chloride | " | " |
| 22 | 2,4-dichloro-5-chloromethyl-6-methylpyrimidine | " | " |
| 23 | 2,4-bismethylsulphonyl-5-chloro-6-methyl- | " | " |

-continued

| | I | II | III |
|---|---|---|---|
| | pyrimidine | | |
| 24 | 2,4,6-trimethyl-sulphonyl-1,3,5-triazine | 1,4-diamino-benzene-2,6-disulphonic acid | " |
| 25 | 3,6-dichloropyridazine-5-carboxylic acid chloride | 1,4-diamino-benzene-2,6-disulphonic acid | 1-(4'-chlorophenyl)-4-sulphomethyl-6-hydroxypyridone-2 |
| 26 | 2,4-dichloropyrimidine-6-carboxylic acid chloride | 1,3-diamino-benzene-4,6-disulphonic acid | 1-(4'-acetaminophenyl)-4-sulphomethyl-6-hydroxypyridone-2 |
| 27 | 2,4,5,6-tetrachloro-pyridazine | " | 1-ethyl-3-cyano-4-sulphomethyl-6-hydroxy-pyridone-2 |
| 28 | 2,4,5,6-tetrafluoropyrimidine | 1,3-diamino-benzene-4-sulphonic acid | " |
| 29 | 2,4,6-trifluoro-5-chloropyrimidine | " | " |
| 30 | 2,4,6-trichloro-1,3,5-triazine | " | " |
| 31 | 2,4-dichloro-6-methylmercapto-1,3,5-triazine | " | " |
| 32 | 2,4-dichloro-6-ethyl-1,3,5-triazine | 1,3-diamino-benzene-4,6-disulphonic acid | 1-phenyl-3-aminocarbonyl-4-sulphomethyl-6-hydroxypyridone-2 |
| 33 | 2,4-dichloro-6-isopropoxy-1,3,5-triazine | " | " |
| 34 | " | 1,3-diamino-benzene-4-sulphonic acid | 1-ethyl-3-aminocarbonyl-4-sulphomethyl-6-hydroxypyridone-2 |
| 35 | " | 1,4-phenylene-diamine-3-sulphonic acid | " |
| 36 | 2-amino-4,6-dichloro-1,3,5-triazine | 1,3-diamino-benzene-4-sulphonic acid | 1-ethyl-4-sulphomethyl-6-hydroxy-pyridone-2 |
| 37 | 2,4,6-trichloro-1,3,5-triazine | " | 4-sulphomethyl-2,6-dihydroxypyridine |
| 38 | 2,4,6-tribromo-1,3,5-triazine | " | 1-ethyl-3-cyano-4-sulphomethyl-6-hydroxypyridone-2 |
| 39 | 2-ethylamino-4,6-dichloro-triazine | " | " |
| 40 | 2-morpholino-4,6-dichloro-triazine | " | " |
| 41 | 2-ureido-4,6-dichloro-triazine | " | " |
| 42 | 2-dimethylamino-sulphonylamino-4,6-dichloro-triazine | " | " |

EXAMPLE 3

To a neutral aqueous solution containing 35.8 parts of the sodium salt of 2-(3'-aminophenyl)amino-4,6-dichloro-1,3,5-triazine-4'-sulphonic acid are added 25 parts by volume of a 4N sodium nitrite solution. The whole mixture is cooled to 0° C and 25 parts by volume of concentrated hydrochloric acid are tipped in all at once. Upon completion of the diazotisation, a slight excess of nitrous acid is annulled by addition of sulphamic acid. Into the suspension of the diazo compound is then poured an aqueous solution containing 23 parts of the sodium salt of 2,6-dihydroxy-4-sulphomethyl-pyridine. The diazo compound passes into solution and a clear yellow dyestuff solution is formed. The pH is adjusted to 7 and then a neutral aqueous solution of 21 parts of the sodium salt of 1,3-phenylenediamine-4-sulphonic acid is added. Condensation is carried out at 20°-25° C, in the course of which the pH of the solution is maintained at 6-7 by the dropwise addition of sodium hydroxide solution. Upon completion of the condensation, the solution is cooled to 0° C and treated with a solution of 18.5 parts of cyanuric chloride in 50 parts of acetone. Condensation is carried out at 0°-5° C, the pH being maintained at 6-7 by the dropwise addition of sodium hydroxide solution. Upon completion of the condensation, 25 parts by volume of a 20% aqueous ammonia solution is added and the batch is stirred for 3 hours at 40° C. The dyestuff of the formula

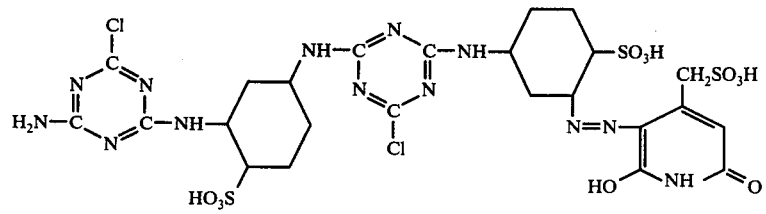

is salted out with sodium chloride, then filtered and dried. It dyes cellulose fibres in fast greenish yellow shades.

EXAMPLE 4

Diazotisation and coupling is carried out as described in Example 3. To the neutral dyestuff solution, which contains the dyestuff of the formula

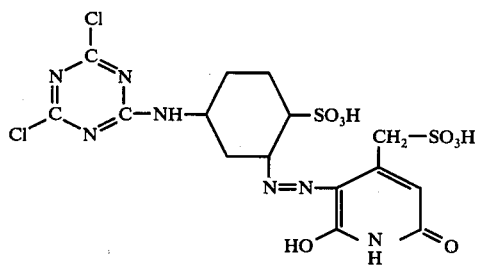

is then added a neutral aqueous solution of 53.3 parts of 1-amino-4-(3'-aminophenyl)-aminoanthraquinone-2,4'-disulphonic acid. The mixture is heated to 40°-45° C and condensation is carried out at this temperature, the pH being maintained at 6-7 by the dropwise addition of sodium hydroxide solution. Upon completion of the condensation, the dyestuff is isolated by addition of sodium chloride. It dyes cellulose fibre fabrics in pure green shades.

If instead of 1-amino-4-(3'-aminophenyl)-aminoanthraquinone-2,4'-disulphonic acid there is used an equivalent amount of the phthalocyanine dyestuff of the formula

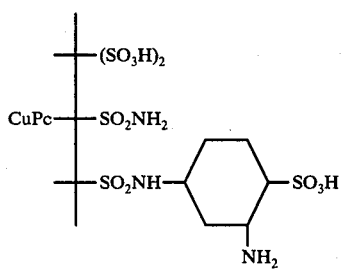

or of the aminoformazane dyestuff of the formula

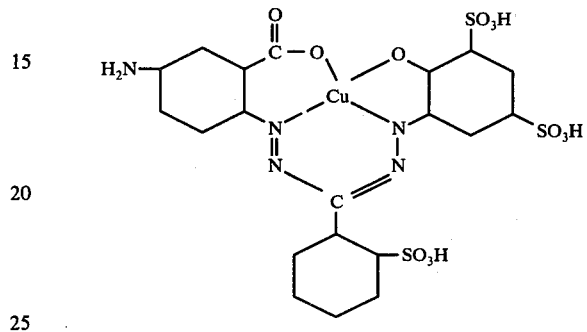

there are obtained likewise dyestuffs which dye cellulose fibre fabrics in fast green shades.

EXAMPLE 5

17.3 Parts of 2-aminobenzenesulphonic acid are dissolved in 100 parts of water with the addition of 5.5 parts of anhydrous sodium carbonate. The resulting solution is treated with 25 parts of volume of 4 normal sodium nitrite solution and the mixture is poured on 100 parts of ice and 25 parts by volume of concentrated hydrochloric acid. The suspension of the diazo compound is adjusted to a pH of 8.5 by addition of 10% sodium carbonate solution. Then 110 parts by volume of an aqueous solution containing 31.2 parts of the sodium salt of 1-ethyl-3-cyano-4-sulphomethyl-6-hydroxypyridone-2 are added and the pH of the reaction mixture is kept at 8.5 to 9 during the coupling. Upon completion of the coupling, the dyestuff is precipitated from the yellow dyestuff solution by addition of sodium chloride. It dyes synthetic polyamide fabric in fast greenish yellow shades.

Further dyestuffs which dye fabrics in the shade indicated in column III of the following Table are obtained according to the directions of the Example by diazotising the diazo components listed in column I and coupling them with the coupling components listed in column II.

|   | I | II | III |
|---|---|---|---|
| 1 | aminobenzene | 1-ethyl-3-aminocarbonyl-4-sulphomethyl-6-hydroxypyridone-2 | yellow on polyamide |
| 2 | 1-amino-4-chlorobenzene | " | " |
| 3 | 1-amino-4-nitrobenzene | " | " |
| 4 | 1-amino-4-methylsulphonylbenzene | 1-methyl-4-sulphomethyl-3-cyano-6-hydroxypyridone-2 | " |
| 5 | 1-amino-2-trifluoromethyl-4-chlorobenzene | " | " |
| 6 | 1-amino-2-chloro-4-methylsulphonylbenzene | " | " |
| 7 | 1-amino-2,2-dicyanobenzene | " | " |

19

-continued

| | I | II | III |
|---|---|---|---|
| 8 | 4-aminobenzoic-cyclohexyl ester | " | " |
| 9 | 1-aminonaphthal-ene-6-sulphonic acid-N,γ-isopropyloxypropylamide | 1-cyano-4-sulphomethyl-2,6-dihydroxy-pyridine | " |
| 10 | 1-aminobenzene-4-sulphonic acid -N-isopropylamide | 3-cyano-4-sulphomethyl-2,6-dihydroxy-pyridine | " |
| 11 | 4-aminophenyl-sulphamate | 1-phenyl-3-acetyl-amino-methyl-6-hydroxypyridone-2 | " |
| 12 | 2-aminothiazole | " | " |
| 13 | 2-aminoquinoline | 1-ethyl-3-cyano-4-sulphomethyl-6-hydroxypyridone-2 | " |
| 14 | 3-amino-6-methyl-benzthiazole | " | orange on polyamide |
| 15 | 2-amino-1,3,5-thiadiazole | " | " |
| 16 | 3-aminobenziso-thiazole | 1-ethyl-4-sulphomethyl-6-hydroxy-pyridone-2 | " |
| 17 | 4-aminoazobenzene | " | " |
| 18 | 4-aminoazobenzene-3'-sulphonic acid | " | " |
| 19 | 4-(6',8'-disulpho-naphth-2'-ylazo)-3-methylaniline | " | " |
| 20 | sulphanilic acid | " | yellow on polyamide |
| 21 | 2-naphthylamine-1-sulphonic acid | 1-benzyl-3-nitroso-4-sulphomethyl-6-hydroxypyridone-2 | " |
| 22 | 1-amino-4-(β-sulphatoethyl-sulphonyl)-benzene | 4-sulphomethyl-2,6-dihydroxypyridine | yellow on cotton |
| 23 | 1-amino-4-(β-sulphatoethyl-sulphonamido)-benzene | 1-ethyl-3-cyano-4-sulphomethyl-6-hydroxypyridone-2 | " |

EXAMPLE 6

65.2 Parts of the disodium salt of the dyestuff of the formula

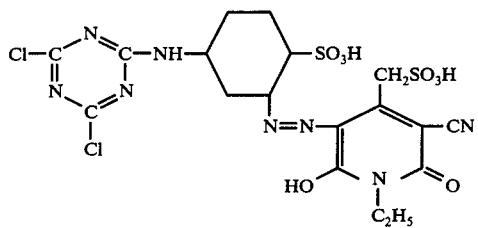

(No. 30 of the Table according to Example 2) are dissolved in 1000 parts of water at pH 7. A solution of 5.4 parts of 1,4-phenylenediamine is added and condensation is carried out at 40°–50° C, in the course of which a pH of 6 to 7 is kept by addition of 2 normal sodium hydroxide solution. Upon completion of the condensation the bis-reactive dyestuff, in which both the reactive groups are linked by a phenylenediamine bridge, is precipitated by addition of sodium chloride. It dyes cotton or regenerated cellulose fibres in pure yellow shades.

A dyestuff with similar properties is obtained by using as bridging component instead of 1,4-phenylenediamine an equivalent amount of 1,3-phenylenediamine, 1,4-phenylenediamine-2-sulphonic acid, 4,4'-diaminostilbene-2,2'-disulphonic acid, 4,4'-diaminodiphenyl-2,2'-disulphonic acid, or 4,4'-diaminodiphenyl urea-3,3'-disulphonic acid.

20

Valuable yellow dyestuffs are also obtained by using as starting material 59.5 parts of the dichlorotriazine dyestuff of the formula

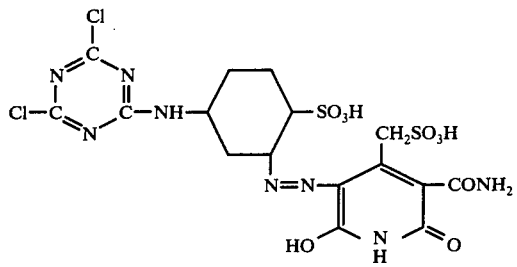

or 55.2 parts of the dyestuff of the formula

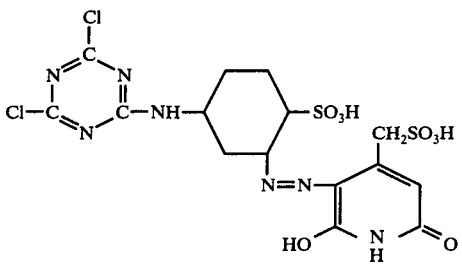

instead of the cited dichlorotriazine dyestuff.

EXAMPLE 7

17.3 Parts of 1-aminobenzene-3-sulphonic acid are dissolved neutral in water by addition of sodium hydroxide solution and condensation with cyanuric chloride is carried out in the conventional manner at 0° to 5° C. Upon completion of condensation an aqueous solution of 21 parts of the sodium salt of 1,3-phenylenediamine-4-sulphonic acid is added and condensation is carried out at 25°–30° C. The batch is subsequently cooled to 0° C, treated with 18.5 parts of cyanuric chloride, and condensation is carried out by the dropwise addition of 2 normal sodium hydroxide solution at pH 4 to 6. Then 21 parts of the sodium salt of 1,3-phenylenediamine-4-sulphonic acid are once more added, the temperature is raised to 30° C, and condensation is carried out at pH 6 to 7. The resulting solution is cooled by addition of ice to 0° C, acidified with 25 parts by volume of 30% hydrochloric acid, and diazotised by the dropwise addition of 4 normal sodium nitrite solution until the permanent blue colouration of potassium iodide starch paper. A solution of 22.6 parts of the sodium salt of 1-ethyl-4-sulphomethyl-6-hydroxypyridone-2 in 100 parts of water is added to the yellow diazo solution. Upon completion of the coupling, neutralisation to pH is carried out by addition of sodium bicarbonate and the dyestuff is precipitated by sprinkling in potassium chloride. It dyes cotton in fast greenish yellow shades.

EXAMPLE 8

12.6 Parts of 6-acetylamino-2-aminophenol-4-sulphonic acid are suspended at 0° C in a mixture of 100 parts of water and 15 parts of 30% hydrochloric acid and diazotisation is carried out by the dropwise addition of 25 parts of 2 normal sodium nitrite solution. The resulting diazo suspension is added to a solution of 12.4 parts of 3-aminocarbonyl-4-sulphomethyl-2,6-dihydroxypyridine in 50 parts of water, 50 parts of ice, and 5.5 parts of 30% sodium hydroxide solution and the pH is slowly adjusted to 7 by the dropwise addition of sodium hydroxide solution. Upon completion of the coupling, 30 parts of 36% hydrochloric acid are added and the batch is refluxed for 1 hour to saponify the acetyl group. The batch is cooled and the dyestuff salted out with sodium chloride. The crystallized dyestuff is filtered off, dissolved in 250 parts of water at pH 7 and the resulting dyestuff solution is treated with a solution of 13 parts of cobalt acetate tetrahydrate. The combined solutions are refluxed for 20 minutes, then allowed to cool, and the cobalt complex is precipitated by addition of sodium chloride. This product is dissolved in 500 parts of water at 35°–40° C and the solution is treated with an aqueous solution of 16.1 parts of 2-phenylamino-4,6-dichlorotriazine-3'-sulphonic acid. Condensation is effected at 35°–40° C, in the course of which a pH of 6 to 7 is kept by the dropwise addition of 2 normal sodium hydroxide solution.

Upon completion of the condensation the dyestuff is precipitated by addition of potassium chloride. It dyes cellulose fibre material in fast reddish orange shades.

A dyestuff which dyes cellulose fibres in fast reddish brown shades is obtained by using an equivalent amount of chromium acetate instead of cobalt acetate.

Manufacturing Examples for Coupling Components

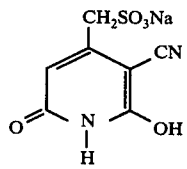

I.

164.5 Parts of γ-chloroacetoacetic ester (obtained by chlorination of diketone and subsequent reaction with ethyl alcohol) are added dropwise at 60° to 70° C over the course of 1 hour to a solution of 130 parts of anhydrous sodium sulphite in 600 parts of water. Stirring is subsequently continued at the indicated temperature until all has passed into solution. Then 84 parts of cyanacetamide are added as well as 87 parts by volume of 25% aqueous ammonia solution and the mixture is refluxed for 16 hours. After it has cooled, the mixture is acidified with concentrated hydrochloric acid to a pH of 2 and the precipitated product is filtered off with suction. Recrystallisation from water yields the pure monosodium salt, which crystallises with 1 mole of water of crystallisation.

| $C_7H_5N_2O_5SNa \cdot H_2O$ | calc. | N 10.36 | S 11.43 |
|---|---|---|---|
| | found | N 10.24 | S 11.42 |

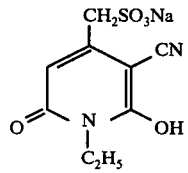

II.

According to the particulars of manufacturing instruction I, γ-chloroacetoacetic ester is reacted first with sodium sulphite. Then 112 parts of cyanoacetic ethylamide are added and 32 parts of ethylenediamine are added as condensation base. The batch is stirred for 20 hours under reflux, allowed to cool, and adjusted to pH 1.5 by addition of concentrated hydrochloric acid, in the process of which the pyridone derivative crystallises out.

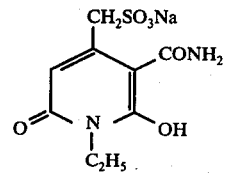

III.

36.9 parts of the compound obtained according to manufacturing instruction II are given to 66 parts by volume of 96% sulphuric acid. The reaction mixture is then stirred for 20 hours at 55° C. After this time no more starting material can be detected by chromatography. The reaction mixture is allowed to cool, poured on 140 parts of ice, and after stirring for 2 hours the precipitated crystalline compound is filtered off with suction.

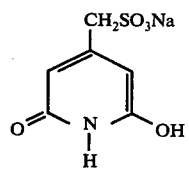

IV.

28 parts of the sodium salt obtained according to manufacturing instruction I are given to a mixture of 25 parts by volume of water and 50 parts by volume of 98% sulphuric acid. The reaction mixture is heated to 125° C and stirred at this temperature until the evolution of carbon dioxide has ceased. The reaction mixture is allowed to cool, diluted with 100 parts of saturated common salt solution, and the product is filtered off with suction.

Dyeing Instruction I 2 parts of the dyestuff of Example 1, 1st. paragraph, are dissolved in 100 parts of water. A cotton fabric is impregnated on a padder with this solution and the excess liquid is squeezed out so that the material retains 75% of its weight of dyestuff solution.

The article so impregnated is dried, then impregnated at room temperature with a solution which contains, per liter, 10 g of sodium hydroxide and 300 g of sodium chloride, squeezed out to 75% liquid pick-up, and steamed at 100° C to 101° C for 60 seconds. The article is then rinsed, soaped at the boil for a quarter of an hour in a 0.3% solution of an ion-free detergent, rinsed, and dried.

Dyeing Instruction II 2 parts of the dyestuff obtained according to Example 1 are dissolved in 100 parts of water.

The solution is added to 3900 parts of cold water, 80 parts of sodium chloride are added, and 100 parts of a cotton fabric are put into this dyebath.

Within 45 minutes the temperature is raised to 80° C, and after 30 minuted 40 parts of trisodium phosphate and a further 80 parts of sodium chloride are added. The temperature is kept for 30 minutes at 80° C, and the fabric is rinsed and then soaped for 15 minutes in a 0.3% boiling solution of an ion-free detergent, then rinsed and dried. A yellow dyeing which is fast to washing and light is obtained.

Printing Instruction

While stirring rapidly, 2 parts of the dyestuff manufactured according to Example 3 are sprinkled into 100 parts of a stock thickening containing 45 parts of 5% sodium alginate thickener, 32 parts of water, 20 parts of urea, 1 part of sodium nitrobenzenesulphonate, and 2 parts of sodium carbonate.

A cotton fabric is printed on a roller printing machine with the resulting printing paste and the printed material is steamed for 4 to 8 minutes at 100° C in saturated steam. The printed fabric is then thoroughly rinsed in cold and hot water, whereby it is possible to remove the non-chemically fixed constituents very easily, and subsequently dried.

I claim:

1. An azo dyestuff of the formula

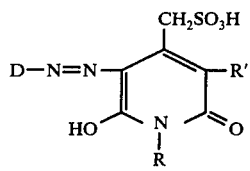

in which
D is phenyl which is unsubstituted or substituted by sulfo, chloro, bromo, methyl, nitro, cyano, methylsulfonyl, trifluoromethyl, carbomethoxy, carboethoxy, hydroxy, amino, ortho methoxy, acetylamino, carboxy, cyclohexyloxycarbonyl, isopropylaminosulfonyl, sulphamato, phenylazo, sulfophenylazo, disulfonaphthylazo or a fiber reactive group capable of reacting with the hydroxy groups of cellulose or the amido groups of polyamide; napthyl substituted by sulfo, acetylamino, γ-isopropyloxypropylaminosulfonyl or hydroxy; thiazole; quinoline; benzthiazole substituted by methyl; 1,3,5-thiadiazole or benzisothiazole;

R is hydrogen; alkyl of 1–4 carbon atoms; β-hydroxyethyl; β-chloroethyl; β-acetylaminoethyl; phenyl which is unsubstituted or substituted by methoxy, chloro or acetamino; benzyl; or a group of the formula —(CH$_2$)$_n$—NH—Z wherein $n$ is 1–4, Z is a fiber reactive group capable of reacting with the hydroxy groups of cellulose or the amido groups of polyamides; and R' is hydrogen, chloro, bromo, cyano, carbonamido, nitro, nitroso, amino, methylsulfonyl or acetylamino.

2. An azo dyestuff according to claim 1, wherein D is said phenyl which is unsubstituted or substituted or is said substituted napthyl,
R is hydrogen or alkyl of 1 to 4 carbon atoms, and
R' is hydrogen, chloro, bromo, cyano or carbonamido.

3. An azo compound according to claim 1 of the formula

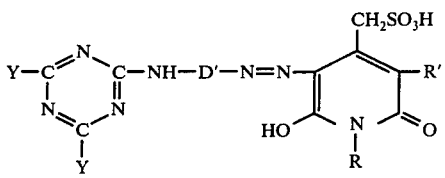

wherein
one Y represents chloro, bromo or fluoro and the other Y represents chloro, bromo, fluoro, amino, ethylamino, ureido, dimethylaminosulfonylamino, phenylamino substituted by sulfo, carboxy, chloroethylsulfonyl or chloroacetylaminomethyl; naphthylamino substituted by sulfo; sulfobenzylamino, N-ω-methane sulfonic acid anilino, morpholino, 6-chloro-4-amino-1,3,5-triazine-2-ylamino-sulfophenylamino, 6-chloro-4-sulfophenylamino-1,3,5-triazine-2-ylamino-phenylamino, 6-chloro-4-sulfophenylamino-1,3,5-triazine-2-ylamino-sulfophenylamino, methoxy, isopropoxy, 1,1-dimethylethoxy, ethoxyethoxy, methoxypropyloxy, phenoxy, sulfophenoxy, disulfophenoxy or methylmercapto;

D' is sulfophenylene which is further unsubstituted or substituted by methyl, chloro or carboxy;

R is hydrogen or alkyl of 1–4 carbon atoms; and

R' is hydrogen, chloro, bromo, cyano or carbonamido.

4. An azo dyestuff according to claim 3, wherein
D' is monosulfophenylene,
R is hydrogen, methyl or ethyl,
R' is cyano, one Y is chloro, bromo or fluoro and the other
Y is mono- or disulfophenylamino, mono- or disulfonapthylamino, methoxy, ethoxyethoxy or isopropoxy.

* * * * *

UNITED STATES PATENT OFFICE
CERTIFICATE OF CORRECTION

Patent No. 4,092,308              Dated May 30, 1978

Inventor(s) Gert Hegar

It is certified that error appears in the above-identified patent and that said Letters Patent are hereby corrected as shown below:

Claim 2, column 24, line 33, delete "1,1-dimethylethoxy" --.

Claim 2, column 24, line 34, delete "methoxypropyloxy" --.

Signed and Sealed this

Third Day of July 1979

[SEAL]

Attest:

LUTRELLE F. PARKER

Attesting Officer      Acting Commissioner of Patents and Trademarks